(12) United States Patent  (10) Patent No.: US 8,873,041 B1
Chai et al.  (45) Date of Patent: Oct. 28, 2014

(54) RAMAN SPECTROSCOPY USING MULTIPLE EXCITATION WAVELENGTHS

(71) Applicant: BaySpec, Inc., San Jose, CA (US)

(72) Inventors: Ming Chai, Union City, CA (US); Wei Yang, Los Altos, CA (US); Chad Lieber, San Jose, CA (US); Miao Yang, Fremont, CA (US); Charlie Zhang, Fremont, CA (US)

(73) Assignee: BaySpec, Inc., San Jose, CA (US)

( * ) Notice: Subject to any disclaimer, the term of this patent is extended or adjusted under 35 U.S.C. 154(b) by 64 days.

(21) Appl. No.: 13/753,150

(22) Filed: Jan. 29, 2013

(51) Int. Cl.
*G01J 3/44* (2006.01)
(52) U.S. Cl.
USPC .......................................................... 356/301
(58) Field of Classification Search
USPC .............................................. 356/301, 72–73
See application file for complete search history.

(56) References Cited

U.S. PATENT DOCUMENTS

| | | | |
|---|---|---|---|
| 5,109,849 | A | 5/1992 | Goodman et al. |
| 5,112,127 | A | 5/1992 | Carrabba et al. |
| 5,700,289 | A | 12/1997 | Breitbart et al. |
| 5,827,181 | A | 10/1998 | Dias et al. |
| 6,048,515 | A | 4/2000 | Kresse et al. |
| 6,108,471 | A | 8/2000 | Zhang et al. |
| 6,167,290 | A | 12/2000 | Yang et al. |
| 6,704,509 | B1 | 3/2004 | Yang et al. |
| 7,102,746 | B2 | 9/2006 | Zhao |
| 7,282,489 | B2 | 10/2007 | Levy et al. |
| 2004/0101822 | A1 | 5/2004 | Wiesner et al. |
| 2005/0027176 | A1 | 2/2005 | Xie |
| 2005/0057749 | A1* | 3/2005 | Dietz et al. ..................... 356/318 |
| 2007/0122829 | A1 | 5/2007 | Ballerstadt et al. |
| 2007/0165236 | A1* | 7/2007 | Haridas ......................... 356/451 |
| 2008/0214913 | A1 | 9/2008 | Van Gogh et al. |
| 2009/0024019 | A1 | 1/2009 | Stein et al. |
| 2012/0099102 | A1* | 4/2012 | Bello ............................ 356/301 |

OTHER PUBLICATIONS

U.S. Appl. No. 13/785,617, Wei Yang, Multiple-Grating High Resolution Spectrometer, filed Mar. 5, 2013.
U.S. Appl. No. 13/800,878, Ming Chai, Multi-excitation Raman Microscope, filed Mar. 13, 2013.
U.S. Appl. No. 13/800,878, non-final Office action, mailed Apr. 1, 2014.
Chellaiah, S., "Nanoparticles find favour in diagnosis, therapy," The Hindu, Nov. 29, 2007, http://www.thehindu.com/thehindu/seta/2007/11/29/stories/2007112950081300.htm.
"Scientists Develop Magnetic Nanoparticle Contrast Agents for Blood Cells," Philips Research, Oct. 2, 2008, www.nano.org.uk/news/oct2008/latest1620.htm.
Adler, R. "Blood cells an raft nanoparticles around the body," New Scientist, Jun. 28, 2007.
"Exploring Nanoparticle Toxicity," National Cancer Institute, Apr. 17, 2006.
Shafer-Peltier, Karen et al., "Toward a glucose biosensor based on surface-enhanced Raman scattering," 2003 J. Am. Chem. Soc. vol. 125, pp. 588-593.

(Continued)

*Primary Examiner* — Abdullahi Nur
(74) *Attorney, Agent, or Firm* — Peters Verny, LLP (57) ABSTRACT

Raman spectrometers are provided that illuminate a sample with two or more different beams of light, each characterized by a different primary frequency. Scattered light from the sample is separated into multiple Raman spectra, one for each primary frequency. The multiple Raman spectra can be evaluated individually, or they can be added together to form a composite spectrum that is then evaluated.

7 Claims, 4 Drawing Sheets

(56) References Cited

OTHER PUBLICATIONS

Stuart, Douglas A., et al., "In Vivo Glucose Measurement by Surface-Enhanced Raman Spectroscopy," Anal. Chem. 2006, 78, 7211-7215.

Qian, Ximei, et al., "In Vivo tumor targeting and spectroscopic detection with surface-enhanced Raman nanoparticle tags," Nature Biotechnology vol. 26, No. 1, Dec. 23, 2007.

Liu, Gang, et al., "Magnetic nanocrescents as controllable surface-enhanced Raman scattering nanoprobes for biomolecular imaging," Advanced Materials, vol. 17, pp. 2683-2688, 2005.

Chamber Elizabeth, et al., "Long circulating nanoparticles via adhesion on red blood cells: Mechanism and extended circulation," Experimental Biology and Medicine, vol. 232, pp. 958-966, 2007.

Sha, Michael, et al., "Surface-enhanced Raman scattering tags for rapid and homogeneous detection of circulating tumor cells in the presence of human whole blood," J. for Am. Chemical Society, vol. 130, pp. 17214-17215, 2008.

McCreery, Richard L. "Raman Spectroscopy for Chemical Analysis," John Wiley & Sons, Inc., ISBN: 0-471-25287-5, Chapter 5, 2000.

"Introductory Raman Spectroscopy," Second Ed., Elsevier Science (USA) Chapters 1 and 2, 1994.

Bowie, B. T., Chase, D. B., and Griffiths, P. R. Factors affecting the performance of bench-top Raman spectrometers: Part 1: Instrumental effects, Applied Spectroscopy (2000a) 54:164A-173A, 2000.

Bowie, B. T., Chase, D. B., and Griffiths. P. R. Factors affecting the performance of bench-top Raman spectrometers: Part 2: Effect of sample, Applied Spectrosoopy (2000b) 54: 200A-207A, 2000.

\* cited by examiner

RAMAN SPECTROSCOPY USING MULTIPLE EXCITATION WAVELENGTHS

BACKGROUND OF THE INVENTION

1. Field of the Invention

The present invention relates generally to Raman spectroscopy and more particularly to systems and methods that utilize more than one incident wavelength to analyze samples.

2. Description of the Prior Art

The Raman spectrum derives from the Raman scattering effect, an effect based on quantum mechanical vibrational levels in a sample. A Raman spectrum is obtained by directing a monochromatic light at a sample and measuring the scattered light as a function of wavelength. The incident light excites molecular vibrations, phonons, and the like, from a ground state to higher quantum levels, and then another photon, shifted in frequency from the incident frequency, is emitted when the system relaxes to the ground state. Peaks in the resulting frequency spectrum provide information about the vibrational modes in the system.

Because the various vibrational energy levels are characteristic of the sample, and not of the apparatus or the excitation, it is possible to create Raman photons using any wavelength of incoming excitation. Therefore, a Raman spectrum generated using any particular excitation wavelength will contain essentially the same spectral bands, though due to resonance, certain Raman bands will present preferentially at certain wavelengths. Although different frequencies of excitation will produce essentially the same set of Raman bands, certain excitation wavelengths are nevertheless more suitable than others for different samples.

As described by Rayleigh's equations, elastic optical scattering is generally proportional to the inverse fourth power of wavelength. For example, the scattering at 1064 nm is 3.4 times less frequent than the scattering at 785 nm. The Raman spectrum is also defined by this criterion, thus selection of the excitation wavelength has a profound effect on the scattering efficiency and resulting intensity of the Raman spectrum, as well as the relative intensities of the Raman bands.

Fluorescence of the sample is another factor in determining a suitable incident wavelength for the measurement of Raman spectra. Fluorescence occurs when electrons in the sample are excited by the incident photons to higher energy levels than those that yield Raman photons. Upon relaxation of these electrons, some emit a fluorescence photon to conserve energy. In general, the proportion of fluorescent photons to Raman photons is several orders of magnitude. In some samples with high fluorescence yields, it is impossible to distinguish any Raman spectral features due to the inordinate fluorescence signal. Because shorter wavelengths contain more energy than longer wavelengths, using shorter incident wavelengths generally causes much more fluorescence than using longer wavelengths. In samples prone to fluorescence such as biological samples, plastics, and dyed samples, it is necessary to select an appropriate Raman excitation wavelength that avoids as much fluorescence as possible.

Figure 1:
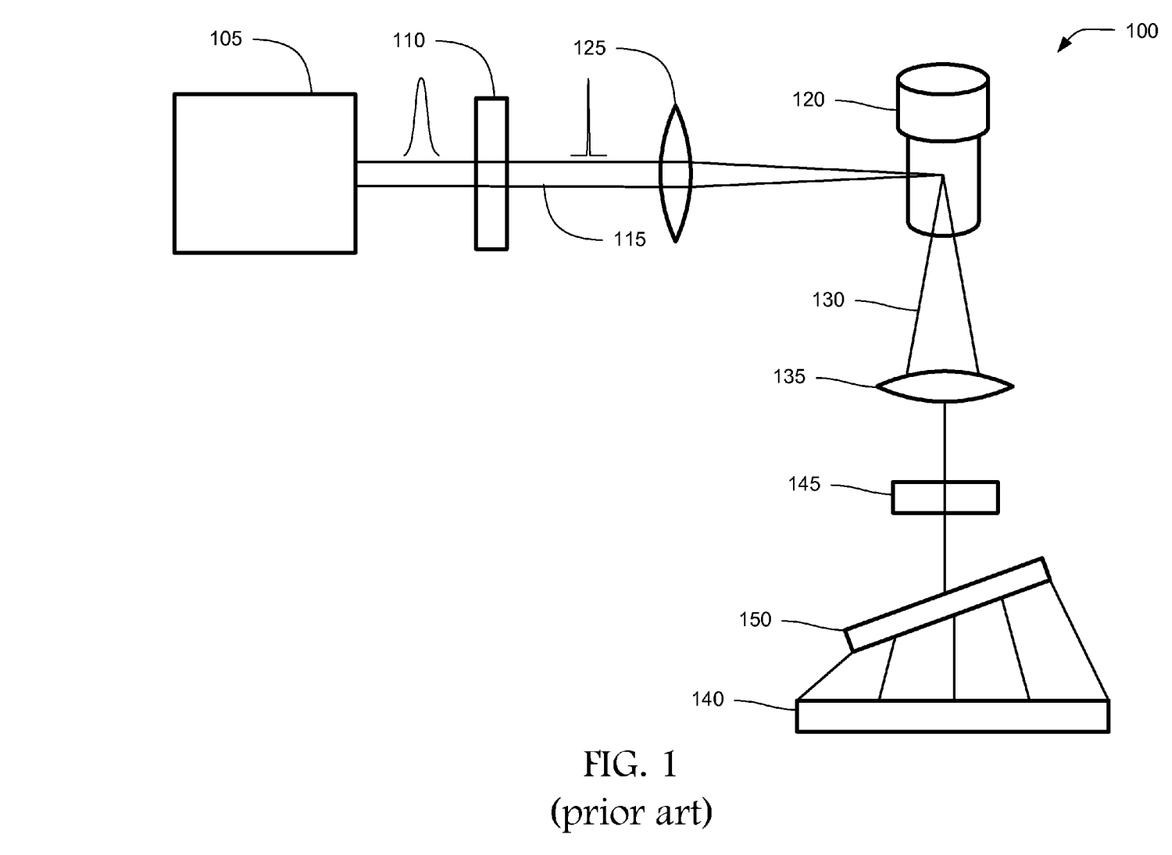
FIG. 1 is a schematic representation of a Raman spectrometer according to the prior art.

FIG. 1 illustrates a Raman spectrometer 100 according to the prior art. The spectrometer 100 includes an excitation source 105, typically a laser such as an optoelectronic diode laser, and a bandpass filter 110 that together produce a beam of light 115 with a very narrow range of frequencies centered on a primary frequency. Other suitable laser excitation sources include solid-state, gas, and liquid laser sources. Additionally, non-laser high-intensity sources can be employed, for example an arc lamp with a wavelength selecting filter. A linewidth of 0.1 nm or less is typical, while high resolution Raman employs a linewidth of 0.01 nm or less. Also, because of the nonlinearity in conversion of wavelength to wavenumbers, the suitable nanometer range in a system using a visible (e.g. green 532 nm) laser is smaller than that of an infrared (e.g. 1064 nm) laser system.

In FIG. 1, the beam 115 is directed onto a sample 120, optionally using a lens system 125 of one or more lenses to bring the beam 115 to a focus on the sample 120, illustrated in the drawing as a vial of a liquid. In some Raman spectrometers 100 a flexible optical waveguide (not shown) is placed between the lens system 125 and the sample 120; the lens system 125 focuses the beam 115 into one end of the waveguide and the other end of the waveguide can be positioned proximate to the sample 120.

Scattered light 130 from the sample 120 is then analyzed. In the spectrometer 100, the scattered light 130 is collected by another lens system 135 that collimates the scattered light 130 towards a detector 140. A filter 145 placed between the lens 135 and the detector 140 removes photons produced by elastic optical scattering, and a wavelength separator 150 directs a specific wavelength to the detector 140. The wavelength separator 150 can be transmissive (as illustrated) or reflective. A second optical waveguide (not shown) can also be employed between the sample 120 and the detector 140, such as between the filter 145 and the wavelength separator 150. A Raman spectrum is obtained by sampling a succession of different wavelengths around the primary frequency. This can be achieved, for example, by tuning the wavelength separator 150 to successive wavelengths over a range of wavelengths and measuring the intensity of the scattered light 130 at each wavelength.

SUMMARY

An exemplary Raman spectroscopy system of the present invention comprises an illumination system and a detection system. The illumination system is configured to direct multiple beams of light onto a same spot on a sample, each beam of light characterized by a spectral linewidth centered on a different frequency. The detection system is configured to receive scattered light from the sample and to produce multiple Raman spectra, one spectrum for each beam of light incident on the sample.

The multiple beams of light, in some embodiments, comprise a first beam of light characterized by a first spectral linewidth centered on a first frequency and a second beam of light characterized by a second spectral linewidth centered on a second frequency, and the illumination system includes a first excitation source configured to produce the first beam of light a second excitation source configured to produce the second beam of light. One or both of the excitation sources can be an optoelectronic diode laser or another high-intensity source such as an arc lamp. In various embodiments the illumination system includes beam-combining optics configured to receive the first and second beams of light and to direct both beams of light into the same optical path. In other embodiments, the illumination system includes a first lens system configured to focus the first beam of light to the spot on the sample and a second lens system configured to focus the second beam of light to the same spot.

The detection system can include a lens system configured to collect scattered light from the sample and to collimate the scattered light into an optical path. In some of these embodiments the detection system further includes a filter disposed along the optical path and configured to receive the collected and collimated scattered light from the lens system and to filter out photons produced by elastic optical scattering. The detection system also includes a spectra separator and can either include a first optical detector and a second optical detector, or just a single optical detector.

In those embodiments that employ a single optical detector, the spectra separator is configured to direct, to a first portion of the optical detector, scattered Raman photons from the received scattered light that were produced by the interaction of the first beam of light with the sample. Similarly, the spectra separator is also configured to direct, to a second portion of the optical detector, scattered Raman photons from the received scattered light that were produced by the interaction of the second beam of light with the sample. The spectra separator, in these embodiments, can comprise a grating, for example.

In embodiments that comprise the two optical detectors, the spectra separator is configured to direct to the first optical detector scattered Raman photons from the received scattered light that were produced by the interaction of the first beam of light with the sample, and further configured to direct to the second optical detector scattered Raman photons from the received scattered light that were produced by the interaction of the second beam of light with the sample. In these embodiments, the detection system can comprise a first grating between the spectra separator and the first optical detector as well as a second grating between the spectra separator and the second optical detector. The spectra separator can comprise, for example, a dielectric dichroic filter. In various embodiments the first optical detector comprises a silicon-based detector and the second optical detector comprises an indium-gallium-arsenide detector.

An exemplary method of the present invention is directed to identify a substance in a sample. The method comprises irradiating a sample with light characterized by a first excitation frequency and also irradiating the sample with light characterized by a second excitation frequency, collecting photons scattered by the sample and generating two Raman spectra therefrom, wherein each generated spectrum is identified to one of the first or second excitation frequencies, and using the first and second spectra to identify a substance in the sample. In various embodiments irradiating the sample with the first and second lights is performed simultaneously, while in other embodiments irradiation with the different lights is performed sequentially. In additional embodiments the difference in wavenumbers between the two excitation frequencies is about 1 nm.

Using the first and second spectra to identify the substance can include matching each spectrum against a library of spectra to determine a best match for each spectrum. In other embodiments, using the first and second spectra to identify the substance includes summing the two spectra to form a composite spectrum and then matching the composite spectrum against the library of spectra to determine a best match. A difference spectrum can also be obtained by subtracting one spectrum from the other, and the difference spectrum can then be matched against the library of spectra.

DETAILED DESCRIPTION OF THE INVENTION

The present invention is directed to Raman spectrometers that illuminate a sample with two or more different beams of light, each beam characterized by a different frequency. The spectrometers of the present invention collect the light scattered from the sample and separate out the resulting Raman photons according to the original beam frequencies to produce a Raman spectrum for each initial beam of light. Methods of the invention are useful to identify substances in the sample. Each resulting Raman spectrum can be compared to known spectra in a library to find one that yields a best match. In some instances, Raman spectra obtained from the sample are added together or a difference between the spectra is obtained, and the resulting composite or difference spectrum is then matched against the library. In some embodiments the several resulting Raman spectra are produced simultaneously, allowing for the study of rapidly changing samples under multiple excitation conditions.

Figure 2:
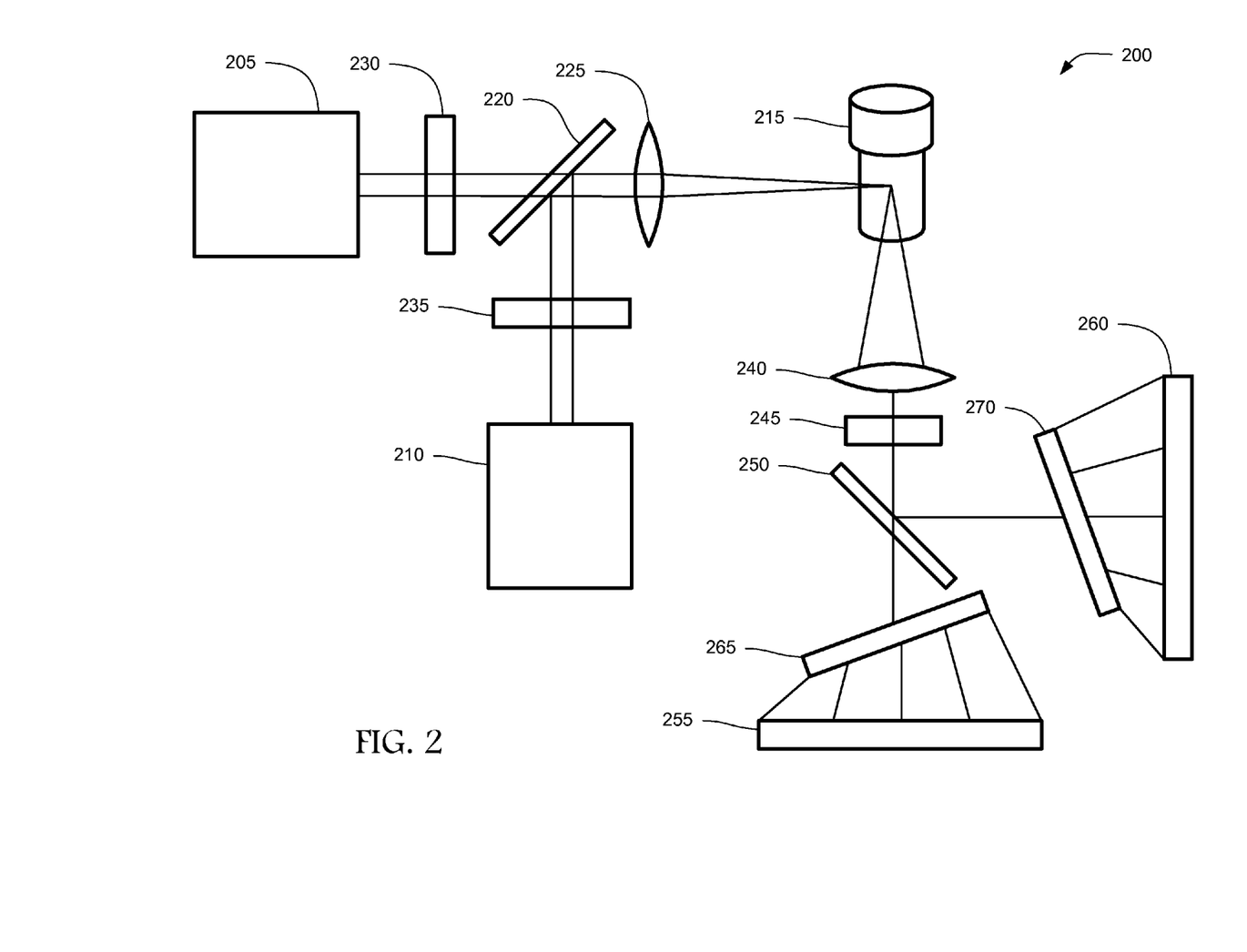
FIG. 2 is a schematic representation of a Raman spectrometer according to an exemplary embodiment of the present invention.

FIG. 2 shows one exemplary embodiment of a Raman spectrometer 200 of the present invention. The spectrometer 200 is generally divided into an illumination system that is configured to direct multiple beams of light onto a same spot on a sample, and a detection system configured to receive scattered light from the sample and produce multiple Raman spectra, one for each beam of light incident on the sample.

In the example of FIG. 2, the illumination system includes a first excitation source 205 and a second excitation source 210, where the first excitation source 205 is configured to produce a first beam of light characterized by a first spectral linewidth centered on a first frequency, and the second excitation source 210 is configured to produce a second beam of light characterized by a second spectral linewidth centered on a second frequency. The frequency that each beam of light is centered upon is referred to herein as the primary or central frequency of the beam. According to the present invention, the spectrometer 200 is not limited to only two excitation sources and could include three or more. The primary frequency of each respective beam of light is different than the primary frequencies of each of the other beams of light, and the primary frequencies are also sufficiently separated in frequency that their respective spectral linewidths do not overlap. Exemplary lasers for the first and second excitation sources 205, 210 include diode lasers that emit at 785 nm, 830 nm, or 1064 nm, argon or diode-pumped solid-state (DPSS) lasers that emit at 532 nm, helium-neon (HeNe) lasers that emit at 633 nm, titanium-sapphire (Ti:Sapph) lasers that are tunable in the 700-900 nm range, and neodymium-doped yttrium aluminum garnet (Nd—YAG) that emit at 1064 nm.

In the example illustrated by FIG. 2 the illumination system is able to direct the beams of light from the excitation sources 205, 210 onto the same spot on a sample 215 by having each excitation source 205, 210 direct its beam of light to beam-combining optics 220 that serve to direct the two beams of light into the same optical path. Additional beam-combining optics 220 can be added to increase the number of excitation sources. Another method of directing multiple beams of light onto the same spot on the sample 215 is described below with reference to FIG. 3.

Beam-combining optics 220 can comprise a dielectric dichroic filter, a grating, a prism, a beamsplitter, an optical circulator, or an optical switch to alternate between excitation wavelengths. In other embodiments, the beam-combining optics 220 can comprise a dense-wavelength-division-multiplexer (DWDM) or a course-wavelength-division-multiplexer (CWDM). Examples of an optical switch as the beam-combining optics 220 includes a mirror configured to move between positions, and an electro-optical component that changes the direction of reflectivity based on a change in an applied voltage. Optical switches, it will be understood, select for which beam of light of the several beams of light will be directed along the optical path at any given time, while other beam-combining optics 220, such as the beamsplitter, serve to bring two or more beams of light into the same optical path simultaneously.

The illumination system of FIG. 2 optionally also includes a lens system 225 of one or more lenses to bring the beams of light from the beam-combining optics 220 to a focus on the sample 215. As discussed below, in some embodiments at least some of the optics of the lens system 225 can also serve as optics within the detection system.

In some embodiments, beams of light produced by the excitation sources 205, 210 are sufficiently narrow that no further filtering is required, and in some of these embodiments the excitation source 205, 210 includes a bandpass filter, or the like, in order to achieve the desired narrowness. In other embodiments, the excitation source 205, 210 produces too wide of a range of frequencies. In some of these embodiments a suitable bandpass filter 230, 235 is placed between each excitation source 205, 210 and the beam-combining optics 220, as illustrated. Alternatively, a single bandpass filter configured to allow two separate frequencies to pass can be place between the beam-combining optics 220 and the sample 215. Bandpass filters described herein can comprise, for instance, a dielectric coating deposited on an optically transparent substrate, or a doped glass that accomplishes optical filtering by means of its selective absorption.

In various embodiments, the beam-combining optics 220 can direct the combined beams into one end of a flexible waveguide such that the other end of the waveguide comprises a probe that can be positioned proximate to the sample 215. In some of these embodiments the probe end of the optical waveguide includes one or more lenses to focus the combined beams of light onto the sample 215. Whether or not an optical waveguide is employed, the lens system 225 can provide beam shaping, such as with a microscope objective lens. Although not shown, some embodiments can include a wavelength-cleaning filter after the optical waveguide to remove any Raman photons generated within the optical waveguide itself.

In the example of FIG. 2, the detection system includes a lens system 240 configured to collect scattered light from the sample 215 and collimate the scattered light. Lens system 240 can include a gradient index lens (GRIN), a reflective focusing minor, or may even be omitted for direct contact with the sample 215. The detection system also optionally includes a filter 245 disposed along the optical path to receive the collected and collimated scattered light from the lens system 240 and to filter out photons produced by elastic optical scattering. Filter 245 can be characterized, in some embodiments, as having a notch or long-pass transmission curve and can comprise, for example, a dielectric coating deposited on an optically transparent substrate, or a doped glass.

In some embodiments, some of the optics of the lens system 240 also form part of the optics of the lens system 225. For example, a parfocal lens can be used to provide excitation to the sample 215 as well as provide collection of scattered light from the sample 215. Such lenses can utilize a wavelength-separating element such as a dielectric dichroic filter to separate the excitation optical path from the collection optical path. In such embodiments, a single probe including the parfocal optics is placed proximate to the sample 215 rather than two, as illustrated in FIG. 2. The parfocal optics can also comprise a microscope objective lens, in some embodiments.

The detection system of FIG. 2 further includes a spectra separator 250 disposed along the optical path to receive the filtered and collimated scattered light from the filter 245, or to receive the collimated scattered light from the lens system 240 in those embodiments in which the filter 245 is not employed. The spectra separator 250 is configured to direct to a first optical detector 255 the scattered Raman photons from the received scattered light that were produced by the interaction of the first beam of light with the sample 215. The spectra separator 250 is likewise configured to direct to a second optical detector 260 the scattered Raman photons from the received scattered light that were produced by the interaction of the second beam of light with the sample 215. Examples of suitable spectra separators 250 include a dielectric dichroic filter, a grating, a prism, or a switch to alternate between collection wavelength regions. Likewise, the spectra separator 250 can comprise a DWDM or CWDM, or an optical switch such as a movable mirror to alternate between the wavelengths. As noted with respect to the beam-combining optics 220, an optical switch when used as the spectra separator is used to select only the scattered light from the interaction of just one beam of light with the sample 215. In some embodiments both the beam-combining optics 220 and the spectra separator 250 comprise optical switches, and in these embodiments the beam from only one excitation source 205, 210 at a time reaches the sample 215 to produce a Raman spectrum, and the optical switches of the beam-combining optics 220 and the spectra separator 250 are coordinated together. In other embodiments the beam-combining optics 220 is of a type that allows more than one beam of light to simultaneously impinge on the sample 215 but the spectra separator 250 comprises an optical switch so that only one spectrum at a time is generated. In still further embodiments neither the beam-combining optics 220 nor the spectra separator 250 comprise optical switches and more than one Raman spectra can be collected simultaneously, as further described below.

The detection system further includes a wavelength separator 265 disposed along the optical path between the spectra separator 250 and the first optical detector 255, and another wavelength separator 270 disposed along the optical path between the spectra separator 250 and the second optical detector 260. An exemplary wavelength separator 265, 270 comprises a spectrograph.

The optical detectors can be single channel or multi-channel detectors, for example. A single-channel detector observes an integrated region of the spectrum during any single exposure, while a multi-channel detector observes multiple discrete regions of the spectrum simultaneously during a single exposure. An appropriate detector material for each optical detector 255, 260 will depend on the primary wavelength it will receive. For example, photons in the visible spectrum from approximately 300 nm to approximately 1100 nm are well detected by silicon-based detectors. Indium-gallium-arsenide (InGaAs) detectors can be employed for wavelengths greater than approximately 1000 nm to approximately 2500 nm. Back-illuminated, deep-depletion silicon-based charge-coupled device (CCD) can also be used to detect within the near-infrared range of approximately 700 nm to approximately 1000 nm. Complementary metal oxide semiconductor (CMOS) optical detectors can also be employed over the near-infrared range of approximately 700 nm to approximately 1000 nm.

Figure 3:
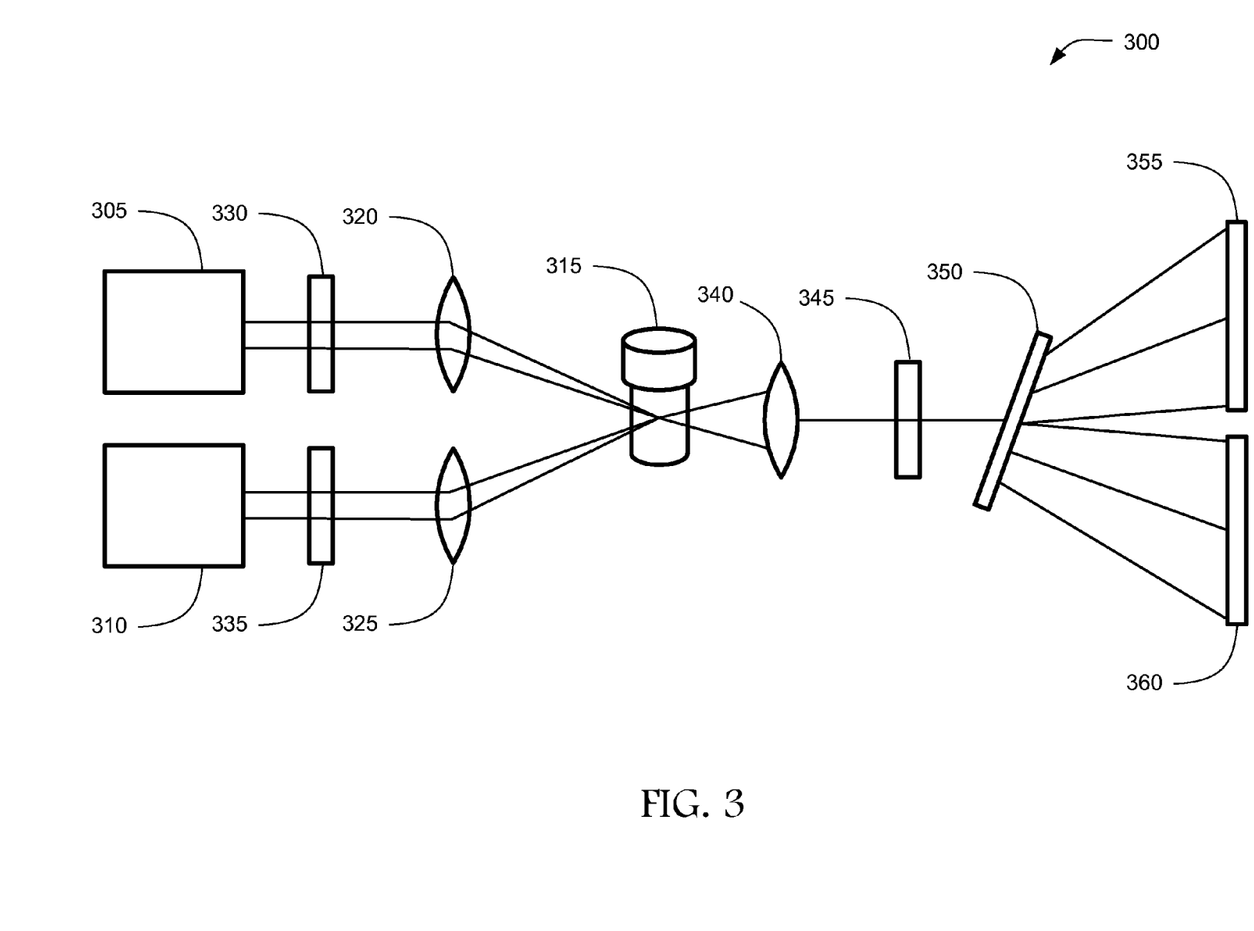
FIG. 3 is a schematic representation of a Raman spectrometer according to another exemplary embodiment of the present invention.

FIG. 3 shows another exemplary embodiment of a Raman spectrometer 300 of the present invention. The spectrometer 300 is also divided into an illumination system configured to direct multiple beams of light onto a same spot on a sample, and a detection system configured to receive scattered light from the sample and produce multiple Raman spectra, one for each beam of light incident on the sample.

In the example of FIG. 3, the illumination system includes a first excitation source 305 and a second excitation source 310, where the first excitation source 305 is configured to produce a first beam of light characterized by a first spectral linewidth centered on a first frequency, and the second excitation source 310 is configured to produce a second beam of light characterized by a second spectral linewidth centered on a second frequency. The spectrometer 300 is not limited to only two excitation sources and could include three or more. The primary frequency of each respective beam of light is different than the primary frequencies of each of the other beams of light, and the primary frequencies are also sufficiently separated in frequency that their respective spectral linewidths do not overlap. It should be noted that in these embodiments, and in the embodiments illustrated with respect to FIG. 2, the excitation sources 305, 310 can produce primary wavelengths that are quite similar, though the spectral linewidths do not overlap. For example, the difference in the primary frequencies can be about 1 nm, in some embodiments, while the linewidths of the beams of light are 0.1 nm or less, or 0.01 nm or less.

In the embodiment illustrated by FIG. 3 the illumination system is able to direct the beams of light from the excitation sources 305, 310 onto the same spot on a sample 315 by directing the beam of light from each excitation source 305, 310 through a lens system 320, 325 where each lens system 320, 325 is configured to focus the received beam of light to the same spot. The illumination system of FIG. 3 can optionally include a suitable bandpass filter 330, 335 placed between each excitation source 305, 310 and their respective lens systems 320, 325. As in the illumination system of the embodiment of FIG. 2, the illumination system of this embodiment can include three or more pairs of excitations sources and lens systems to direct more than two beams of light onto the same spot on the sample 315.

The detection system of the embodiment of FIG. 3 includes a lens system 340 configured to collect scattered light from the sample 315 and to collimate the scattered light. The detection system also optionally includes a filter 345 disposed along the optical path to receive the collected and collimated scattered light from the lens system 340 and to filter out photons produced by elastic optical scattering.

The detection system of FIG. 3 further includes a spectra separator 350 disposed along the optical path to receive the filtered and collimated scattered light from the filter 345, or to receive the collimated scattered light from the lens system 340 in those embodiments in which the filter 345 is not employed. The spectra separator 350 is configured to direct to a first optical detector 355 the scattered Raman photons from the received scattered light that were produced by the interaction of the first beam of light with the sample 315. The spectra separator 350 is likewise configured to direct to a second optical detector 360 the scattered Raman photons from the received scattered light that were produced by the interaction of the second beam of light with the sample 315. In these embodiments, the spectra separator 350 can be a grating, for example.

Still further embodiments employ a single optical detector in place of the first and second optical detectors. In these embodiments the spectra separator 350 directs the scattered Raman photons from the received scattered light that were produced by the interaction of the first beam of light with the sample 315 to a first portion of the single optical detector. Likewise, the single spectra separator 350 directs the scattered Raman photons from the received scattered light that were produced by the interaction of the second beam of light with the sample 315 to a second portion of the single optical detector. In embodiments that employ more than two excitation sources, it is possible to use multiple spectra separators 350 and various combinations of optical detectors each dedicated to an individual spectrum and optical detectors that detect two or more of the spectra.

It will be appreciated that in still other embodiments the detection system of FIG. 3 can be paired with the illumination system of FIG. 2, and the detection system of FIG. 2 can likewise be paired with the illumination system of FIG. 3. Although the present invention provides systems with more than one excitation source and more than one optical detector, it will be appreciated that each excitation source and detector pair can operate independently in some embodiments such that two or more can operate simultaneously or only one at a time. Accordingly, in those instances where an excitation frequency of one of the excitation sources 205, 210 (FIG. 2) or 305, 310 (FIG. 3) is known to be optimal for a particular type of sample, the other excitation source is not used and only one Raman spectrum is obtained.

The systems of the present invention also include logic (not shown) configured to receive data from the several optical detectors, reduce the data to resolve the Raman spectra, and to compare spectra against libraries of previously stored standard Raman spectra from known substances. These comparisons can include generating a figure of merit to describe the degree to which a collected spectrum matches a standard spectrum in order to rank the standard spectra to establish a best match, a second best match, and so forth. The logic, in some embodiments, can also add two or more collected spectra to produce a composite spectrum that can be compared to a library of standard spectra. The logic, in still other embodiments, can also determine a difference between spectra, for example, to detect the presence or absence of a trace level contaminant within a mixture, or to provide simple classification between two very similar samples.

Figure 4:
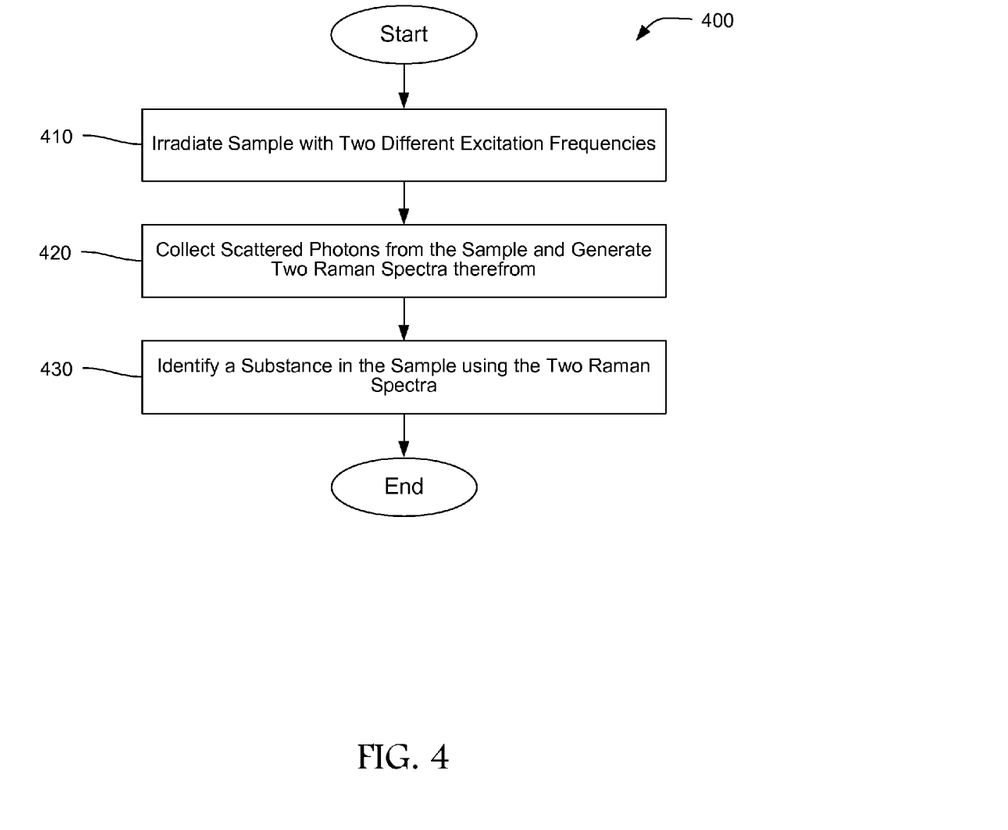
FIG. 4 is a flowchart representation of a method according to an exemplary embodiment of the present invention.

Methods of the present invention provide ways to employ Raman spectra generated by multiple excitation frequencies, as illustrated by the exemplary method 400 of FIG. 4. According to various embodiments of the present invention, in a step 410 a sample is irradiated with light characterized by a first excitation frequency and also irradiated with light characterized by a second excitation frequency, either simultaneously or successively. Step 410 can include generating two beams of light and directing the two beams of light onto a same spot on the sample. While each beam of light is produced by a separate excitation source, in some embodiments each beam of light is directed onto a common optical path to reach the sample. In other embodiments each beam of light traverses a different optical path to the sample.

Next, in a step 420, photons scattered by the sample are collected and at least two Raman spectra are generated from the scattered photons, where each spectrum is identified to one of the first or second excitation frequencies.

In a step 430 the two Raman spectra are used to determine a substance in the sample, where a substance can be a pure compound or mixture, for example. In some embodiments, each Raman spectrum is compared to a library of Raman spectra and one or more matches for each spectrum are determined. If both spectra match the same standard spectrum then the substance is determined to be the substance identified to the standard. In some instances, each collected Raman spectrum will produce a best match to a different standard. In these instances the collected Raman spectrum that is scored as matching more highly to the standard spectrum can be selected and the substance of the sample identified as the substance of that standard.

In other embodiments, step 430 includes adding together two or more Raman spectra, and the resulting spectrum is compared to the library of Raman spectra to produce one or more best matches. The substance is determined to be the substance identified to the standard that produced the best match. Likewise, step 430 can also include subtracting one Raman spectrum from another to create a difference spectrum, and then the difference spectrum is compared to the library of Raman spectra to produce one or more best matches.

Subtracting two Raman spectra measured at very small (e.g. ~1 nm) changes in the primary frequencies of the excitation effectively creates a derivative of the Raman spectrum that eliminates the less wavelength-sensitive fluorescence background, a technique called Shifted Excitation Raman Difference Spectroscopy (SERDS). Subtraction also can show differences between two spectra that could be used for simple discrimination, or to detect small changes in the spectra, such as those when a trace level of a substance is present in a larger mixture.

Methods of the invention in which two or more beams of light from two or more excitation sources reach the sample simultaneously and produce two or more Raman spectra simultaneously are well suited for analyzing rapidly changing samples. Examples where change in a sample can be rapid include chemical reactions and phase changes, for instance pharmaceutical lypholization and combustion analyses. In these situations Raman spectra created from different excitation sources but collected sequentially may not be comparable.

The various examples of logic noted above can comprise hardware, firmware, or software stored on a computer-readable medium, or combinations thereof. A computer-readable medium, as used herein, expressly excludes paper and carrier waves. Computer implementation of method steps noted herein can comprise executing a set of instructions stored on a computer-readable medium that cause the step to be carried out. A computing system programmed to perform particular functions pursuant to instructions from program software is a special purpose computing system for performing those particular functions. Data that is manipulated by a special purpose computing system while performing those particular functions is at least saved in electronic buffers of the computing system, physically changing the special purpose computing system from one state to the next with each change to the stored data. Claims directed to methods herein are expressly limited to computer-implemented embodiments thereof and expressly do not cover embodiments that can be performed purely mentally.

In the foregoing specification, the invention is described with reference to specific embodiments thereof, but those skilled in the art will recognize that the invention is not limited thereto. Various features and aspects of the above-described invention may be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A Raman spectroscopy system comprising: an illumination system configured to direct multiple beams of light onto a same spot on a sample, each beam of light characterized by a spectral linewidth centered on a different frequency, the illumination system including a diode laser configured to produce a first beam of light, of the multiple beams of light, the first beam of light characterized by a first spectral linewidth centered on a first frequency of either about 785 nm or about 830 nm, and a neodymium-doped yttrium aluminum garnet laser configured to produce a second beam of light, of the multiple beams of light, the second beam of light characterized by a second spectral linewidth centered on a second frequency of about 1064 nm, a first lens system configured to focus the first beam of light to the spot on the sample, the first lens system being configured to direct the first beam of light along a first optical path defined between the first lens system and the spot, and a second lens system configured to focus the second beam of light to the spot on the sample, the second lens system being configured to direct the second beam of light along a second optical path defined between the second lens system and the spot, the first and second optical paths being different; and a detection system configured to receive scattered light from the sample and produce multiple Raman spectra, one spectrum for each beam of light incident on the sample, the detection system including a first optical detector and a second optical detector, where the first optical detector comprises a silicon-based detector and the second optical detector comprises an indium-gallium-arsenide detector.

2. The Raman spectroscopy system of claim 1 wherein the detection system includes a lens system configured to collect scattered light from the sample and to collimate the scattered light into an optical path.

3. The Raman spectroscopy system of claim 2 wherein the detection system further includes a filter disposed along the optical path and configured to receive the collected and collimated scattered light from the lens system and to filter out photons produced by elastic optical scattering.

4. The Raman spectroscopy system of claim 1 wherein the detection system further includes a spectra separator configured to
    direct to the first optical detector scattered Raman photons from the received scattered light that were produced by the interaction of the first beam of light with the sample, and further configured to
    direct to the second optical detector scattered Raman photons from the received scattered light that were produced by the interaction of the second beam of light with the sample.

5. The Raman spectroscopy system of claim 4 further comprising a grating between the spectra separator and the first optical detector.

6. The Raman spectroscopy system of claim 5 wherein the spectra separator comprises a dielectric dichroic filter.

7. The Raman spectroscopy system of claim 4 wherein the spectra separator comprises a grating.

* * * * *